(12) United States Patent
Kerrigan et al.

(10) Patent No.: US 8,821,958 B2
(45) Date of Patent: *Sep. 2, 2014

(54) METHOD FOR ELECTROSTATIC COATING OF A STENT

(75) Inventors: Cameron K. Kerrigan, Burlingame, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/600,125

(22) Filed: Aug. 30, 2012

(65) Prior Publication Data
US 2012/0321778 A1    Dec. 20, 2012

Related U.S. Application Data

(63) Continuation of application No. 12/464,602, filed on May 12, 2009, now Pat. No. 8,298,607, which is a continuation-in-part of application No. 12/121,692, filed on May 15, 2008, now abandoned.

(51) Int. Cl.
| | | |
|---|---|---|
| A61L 33/00 | (2006.01) | |
| A61K 9/50 | (2006.01) | |
| B05D 1/04 | (2006.01) | |
| A61F 2/06 | (2013.01) | |
| A61L 31/16 | (2006.01) | |
| A61L 31/14 | (2006.01) | |

(52) U.S. Cl.
CPC ............ *A61L 31/16* (2013.01); *A61L 2300/416* (2013.01); *A61L 31/14* (2013.01); *A61L 2300/606* (2013.01); *A61L 2420/02* (2013.01)
USPC ......... 427/2.25; 427/2.1; 427/2.21; 427/2.24; 427/458; 623/1.1

(58) Field of Classification Search
CPC A61B 19/04; A61L 29/085; A61L 2300/404; A61L 31/16; A61L 31/10; A61F 2/91
USPC ........ 427/2.21, 2.1, 2.24, 458, 476, 457, 486, 427/2.25; 623/1.15, 1.1, 1.17, 1.18, 1.19, 623/1.2; 424/428, 426, 423
See application file for complete search history.

(56) References Cited

U.S. PATENT DOCUMENTS 6,329,386 B1    12/2001    Mollison
6,620,463 B2    9/2003    Stay
(Continued)

FOREIGN PATENT DOCUMENTS

WO    WO 01/49340    7/2001
WO    WO 2004/103428    12/2004
(Continued)

OTHER PUBLICATIONS
U.S. Appl. No. 12/121,692, filed May 15, 2008, Kerrigan.
(Continued)

*Primary Examiner* — Bijan Ahvazi
*Assistant Examiner* — Atnaf Admasu
(74) *Attorney, Agent, or Firm* — Squire Patton Boggs (US) LLP

(57) ABSTRACT

A method for electrostatic coating of medical devices such as stents and balloons is described. The method includes applying a composition to a polymeric component of a medical device which has little or no conductivity. The polymeric component could be a material from which the body or a strut of the stent is made or could be a polymeric coating pre-applied on the stent. The polymeric component could be the balloon wall. A charge can then be applied to the polymeric component or the polymeric component can be grounded. Charged particles of drugs, polymers, biobeneficial agents, or any combination of these can then be electrostatically deposited on the medical device or the coating on the medical device. One example of the composition is iodine, iodine, iodide, iodate, a complex or salt thereof which can also impart imaging capabilities to the medical device.

11 Claims, 1 Drawing Sheet

(56) References Cited

U.S. PATENT DOCUMENTS

| | | |
|---|---|---|
| 6,669,980 B2 | 12/2003 | Hansen |
| 6,743,463 B2 | 6/2004 | Weber et al. |
| 6,855,429 B2 | 2/2005 | Stay |
| 7,449,210 B2 * | 11/2008 | Malik et al. ............... 427/2.1 |
| 7,959,942 B2 * | 6/2011 | Cottone ..................... 424/428 |
| 2004/0185168 A1 | 9/2004 | Weber et al. |
| 2004/0213893 A1 | 10/2004 | Boulais |
| 2004/0260379 A1 | 12/2004 | Jagger et al. |
| 2006/0136048 A1 | 6/2006 | Pacetti et al. |
| 2006/0142838 A1 | 6/2006 | Molaei et al. |
| 2006/0216431 A1 | 9/2006 | Kerrigan |
| 2007/0162110 A1 | 7/2007 | Dave |
| 2007/0224244 A1 | 9/2007 | Weber et al. |
| 2008/0009939 A1 | 1/2008 | Gueriguian et al. |
| 2012/0328769 A1 | 12/2012 | Kerrigan et al. |

FOREIGN PATENT DOCUMENTS

| | | |
|---|---|---|
| WO | WO 2005/014069 | 2/2005 |
| WO | WO 2005/077542 | 8/2005 |
| WO | WO 2005/115496 | 12/2005 |
| WO | WO 2006/060033 | 6/2006 |

OTHER PUBLICATIONS

Tepe et al., "Local Delivery of Paclitaxel to Inhibit Restenosis during Angioplasty of the Leg", N. Engl. J. of Med. 358, pp. 689-699 (2008).

Werk et al., "Inhibition of Restenosis in Femoropopliteal Arteries, Paclitaxel-Coated Versus Uncoated Ballon: Remoral Paclitaxel Randomized Pilot Trial", downloaded from circ.ahajournals.org on Aug. 19, 2009, pp. 1358-1365.

Unverdorben "The Paclitaxel-Eluting PTCA-Balloon Catheter in Coronary Artery Disease", Clinical Res. Inst. PEPCAD I/II TCT, 2007, 22 pgs.

RIDAFOROLIMUS, Statement on a Nonproprietary Name Adopted by the USAN Council, 1 page.

ZOTAROLIMUS, Statement on a Nonproprietary Name Adopted by the USAN Council, 2 pages.

* cited by examiner

METHOD FOR ELECTROSTATIC COATING OF A STENT

CROSS REFERENCE

This application is a continuation application of U.S. application Ser. No. 12/464,602, filed on May 12, 2009, published as United States Application Publication number 2009-0285974 A1 on Nov. 19, 2009, and issuing as U.S. Pat. No. 8,298,607 B2, on Oct. 30, 2012, and the entire content of U.S. application Ser. No. 12/464,602, including any drawings, is incorporated by reference herein; and U.S. application Ser. No. 12/464,602 is a continuation-in-part of U.S. application Ser. No. 12/121,692, filed on May 15, 2008, now abandoned, and the entire content of U.S. application serial number 12/121,692 is incorporated by reference.

FIELD OF INVENTION

The present invention is related to methods of electrostatically coating a medical device, more specifically a stent or a balloon. More particularly, the present invention is related to methods of electrostatically depositing drugs or active agents on polymeric stents, polymeric coatings on stents, polymeric dilatation balloons, or other medical devices.

BACKGROUND OF THE INVENTION

In percutaneous transluminal coronary angioplasty (PTCA), a balloon catheter is inserted through a brachial or femoral artery, positioned across a coronary artery occlusion, and inflated to compress against atherosclerotic plaque to open, by remodeling, the lumen of the coronary artery. The balloon is then deflated and withdrawn. Problems with PTCA include formation of intimal flaps or torn arterial linings, both of which can create another occlusion in the lumen of the coronary artery. Moreover, thrombosis and restenosis may occur several months after the procedure and create a need for additional angioplasty or a surgical by-pass operation. To address these issues, stents, which are small, intricate, implantable medical devices, play an important role in PTCA. Stents are generally implanted to reduce occlusions, inhibit thrombosis and restenosis, and maintain patency within vascular lumens such as, for example, the lumen of a coronary artery.

Stents are often modified to provide drug delivery capabilities to further address thrombosis and restenosis. Stents are being coated with a polymeric carrier impregnated with a drug or therapeutic substance. A conventional method of coating includes applying a composition including a solvent, a polymer dissolved in the solvent, and a therapeutic substance dispersed in the blend to the stent by immersing the stent in the composition or by spraying the composition onto the stent. The solvent is allowed to evaporate, leaving on the stent strut surfaces a coating of the polymer and the therapeutic substance impregnated in the polymer. However, dipping and spraying techniques requires for large amounts of drugs and solvents to be used which can be hazardous for the operator and the environment.

An additional new venue for intravascular therapy is the drug coated balloon. These devices are dilatation balloons equipped with a drug containing coating. This coating consists of a therapeutic drug(s) combined with a polymeric carrier or excipient which may be released into the bloodstream. During peripheral angioplasty, commonly known as percutaneous transluminal angioplasty (PTA), a balloon dilation is performed, to dilate an occlusive lesion, with the drug present on the outer coating layer of the balloon. PTA is most commonly used to treat narrowing of the leg arteries, especially, the iliac, external iliac, superficial femoral and popliteal arteries. PTA can also treat narrowing of veins, and other blood vessels. The drug containing outer coating is then transferred to the inner wall of the blood vessel. The function of the transferred drug coating is to reduce restenosis, or other undesirable sequelae of the procedure. Drug coated balloons with paclitaxel are presently approved for use in treatment of the coronary arteries. However, drug coated balloons are being heavily considered for use in the peripheral vasculature as shown by the results of the THUNDER and FemPac clinical trials. (Tepe G, et al. N Eng J Med, 358; 7, 2008, p 689; Werk M, et al. Circ. 2008; 118: 1358-1365.)

Furthermore, in a study which evaluated restenosis and the rate of major adverse cardiac events (MACE) such as heart attack, bypass, repeat stenosis, or death in patients treated with drug eluting balloons and drug eluting stents, the patients treated with drug eluting balloons experienced only 3.7 percent restenosis and 4.8 percent MACE as compared to patients treated with drug eluting stents, in which restenosis was 20.8 percent and 22.0 percent MACE rate. (PEPCAD I/II, M. Unverdorben, TCT, October 2007).

One of the putative advantages of PTA balloons is the minimization of restenosis after stent implantation. In some PTCA cases, it was found that within about six months of stenting, a re-narrowing of the blood vessel characterized by a growth of smooth muscle cells often persisted. Restenosis was discovered to be a "controlled injury" of the angioplasty procedure and was analogous to a scar forming over an injury. Drug eluting stents (DES) is one of the solutions to address restenosis by the use of anti-proliferative and/or cytostatic drugs to interfere with the vessel cell growth and migration processes.

There are several current theories about the mechanism by which a drug coated balloon transfers drug to the vessel wall. One theory, for example, is that upon balloon expansion, drug mechanically fractures or dissolves from the coating, diffuses to the vessel wall and then permeates into the vessel wall. A second theory is that upon balloon expansion the balloon coating is transferred to the vessel wall, and then drug permeates into the vessel wall from the coating adhered to the vessel wall. Another theory is that the balloon expansion creates tears and microfissures in the vessel wall and a portion of the coating inserts into the tears and microfissures. Drug then permeates into the vessel wall from the coating within the tears and fissures. Yet another theory is that upon balloon expansion, a layer of dissolved drug and coating excipients is formed at a high concentration on the vessel wall as a boundary layer. Thus it would be advantageous to have a consistent uniform coating applied to the balloon surface. One that is formulated to exhibit one of the above properties.

The current dipping and spray techniques are very wasteful methods of coating medical devices, most particularly when very small geometrical structures like stents are being coated. For example, during the spray application of the drug composition, a majority of the coating material, including a drug, is wasted as only a fraction of the spray flux is intercepted by the stent struts. Considering that the pharmaceutical agents are costly, it would be beneficial to reduce coating process waste.

Moreover, dipping and spray coating processes can tend to promote a great deal of coating defects. Coating defects can include an uneven thickness in stent and balloon coating, which would in effect translate into uneven distribution of the drug across the surface body of the medical device. Stent coating defects can also include "webbing" between stent struts (over the gaps or opening between the struts) or coating "pools" which are excessive gatherings on the stent struts. Webbing and pooling can lead to adverse biological responses when the stent is implanted. A coating process which reduces or eliminates coating defects and is more superior than the conventional coating processes would be very desirable.

Finally, dipping and spray coating processes can lead to manufacturing inconsistencies between batches of stents and balloons during production. Lack of control in the coating process can lead to, for example, an unpredictable drug distribution and inconsistent coating topography between different batches of stents or balloons. An unpredictable drug distribution means that some stents can have more drug than was intended to be deposited and some can have significantly less. When coating balloons, a uniform coating is desired in order to treat the vessel uniformly. The possibility of treating the lesion in a more uniform manner is one potential advantage for a drug coated balloon versus a stent. Furthermore, drug transfer from the balloon to the vascular wall tissue and occurs within one minute, and preferably within 30 seconds upon inflation of the balloon. Therefore, a need exists for consistent and uniform drug coating to facilitate efficient drug transfer to all areas of the vessel wall that is in contact with the balloon surface. A large discrepancy in what was intended to be deposited is definitely unwanted since it will not be known with accuracy how much drug a patient will receive. Inconsistent coating topography means that the release rate of the drug from stent-to-stent can vary. Again, it is obviously more desirable to be able to accurately provide, with a very small differential in the mean deviation, the average release rate of the drug from the stent or balloon being manufactured.

All manufacturers have invested a great amount of research in improving their coating techniques. One proposed method has been by electrostatic deposition, such as that disclosed in U.S. application Ser. No. 11/093,166, to Cameron K. Kerrigan, which is incorporated herein by reference. Electrostatic coating techniques are well known in the art. Particles of a drug are charged. The stent is grounded or is oppositely charged. The electrostatic attraction between the stent and drug results in a more efficient drug deposition, with less waste and more consistent coating characteristics. This is particularly beneficial for stents which have a very complex, three dimensional tubular structure, with struts separated from each other by gaps. Dilatation balloons, particularly for the peripheral vessels, can be quite large, up to 8×100 mm in size. Coating these large medical devices can consume large quantities of drug making an efficient coating process highly desirable.

Stents that are made from metallic materials provide for conductive surfaces which can be easily charged for electrostatic deposition. However, stents that have been pre-coated with a polymer, for example a polymer primer without a drug, or those that are made from a polymer provide for electrically non-conductive surfaces and cannot be grounded, biased or polarized for electrostatic deposition of drugs. Furthermore, all dilatation balloons are composed of polymeric materials, and as such are generally non-conductive. These polymers also cannot be grounded or biased to allow electrostatic deposition.

The present invention provides for methods of electrostatic coating of polymeric stents, stents that include a polymeric coating, or dilatation balloons of insufficient conductivity to be able to efficiently deposit a drug or other material.

SUMMARY

A method of manufacturing a drug coated medical device, e.g., stent or balloon, is provided, comprising mounting the device on a support structure, the device being made from or including a polymeric material having insufficient conductivity for electrostatic coating; applying iodine, iodide, iodate, a complex or salt thereof to the surface of the device; grounding the device or applying a first charge to the device after the application of the iodine, iodide, iodate, the complex or salt thereof to the surface of the device; and applying a charged drug to the device such that the drug is electrostatically deposited on the device. In some embodiments, the amount of iodine, iodide, iodate, the complex or the salt thereof is of an amount that allows for visualization of the stent or balloon by the physician during the procedure. The iodine, iodide, iodate, the complex or salt thereof can be dissolved in a solvent and applied to the surface of the device. The solvent can be removed prior to the application of the charged drug to the device. Alternatively, the surface of the device is wet during the application of the charged drug to the device.

The method can also including applying a charged polymer contemporaneously with the application of the charged drug or prior to the application of the drug. The drug can be an anti-proliferative or cytostatic agent such as rapamycin, methyl rapamycin, everolimus, 42-Epi-(tetrazoylyl)rapamycin (ABT-578, zotarolimus), biolimus, temsirolimus, novolimus, myolimus, deforolimus, tacrolimus, paclitaxel, protaxel, taxanes, docetaxel, estradiol, clobetasol, idoxifen, tazarotene and any prodrugs, metabolites, analogs, homologues, congeners, and any derivatives, salts and combinations thereof. The therapeutic agents can also include anti-inflammatory, antineoplastic, antiplatelet, anti-coagulant, anti-fibrin, antithrombotic, antimitotic, antibiotic, antiallergic and antioxidant compounds. Thus, the therapeutic agent can be, without limitation, a synthetic inorganic or organic compound, a protein, a peptide, a polysaccharides and other sugars, a lipid, DNA and RNA nucleic acid sequences, an antisense oligonucleotide, an antibody, a receptor ligand, an enzyme, an adhesion peptide, a blood clotting agent including streptokinase and tissue plasminogen activator, an antigen, a hormone, a growth factor, a ribozyme, and a retroviral vector.

In accordance with another aspect of the invention, a method of coating a stent is provided comprising mounting a stent on a support structure, the stent including a polymeric component; applying a treatment material including a halogen, halogen salt, halogen complex or a moiety including a halide, to the polymeric component; grounding the polymeric component or applying a charge to the polymeric component; and applying a charged drug to the polymeric component such that the drug is electrostatically deposited on the stent. The treatment material is iodine, iodide, iodate, a complex or salt thereof. The treatment material can be dissolved in a solvent. In some embodiments, the treatment material consists of iodine iodide, iodate, a complex or salt thereof dissolved in a solvent system. The polymeric component can be the material from which a strut of the stent is made. The polymeric component can be biodegradable to allow the stent to be eliminated from the patient after a period of time. The polymeric component can be a coating on the surface of the stent. In some embodiments, the treatment material includes a solvent such that the charged drug is applied only after the solvent has been removed. Alternatively, the charged drug is applied prior to the removal of the solvent and when the polymeric component is wet.

In accordance with another aspect of the invention, a method of coating a balloon is provided comprising mounting a balloon on a support or contacting element, the balloon including a polymeric component; applying a treatment material including a halogen, halogen salt, halogen complex or a moiety including a halide, to the polymeric component;

grounding the polymeric component or applying a charge to the polymeric component; and applying a charged drug to the polymeric component such that the drug is electrostatically deposited on the balloon. The treatment material is iodine, iodide, iodate, a complex or salt thereof. The treatment material can be dissolved in a solvent. In some embodiments, the treatment material consists of iodine iodide, iodate, a complex or salt thereof dissolved in a solvent system. The polymeric component can be the material from which the balloon is made. The polymeric component can be a coating on the surface of the balloon. In some embodiments, the treatment material includes a solvent such that the charged drug is applied only after the solvent has been removed. Alternatively, the charged drug is applied prior to the removal of the solvent and when the polymeric component is wet.

A medical device may be any suitable substrate that can be implanted permanently or temporarily in a human or non-human animal. Examples of medical devices include, but are not limited to, self-expandable stents, balloon-expandable stents, coronary stents, peripheral stents, stent-grafts, dilatation balloons, angioplasty balloons, catheters, other expandable tubular devices for various bodily lumen or orifices, grafts, vascular grafts, arterio-venous grafts, by-pass grafts, pacemakers and defibrillators, leads and electrodes for the preceding, artificial heart valves, anastomotic clips, arterial closure devices, patent foramen ovale closure devices, cerebrospinal fluid shunts, and particles (e.g., drug-eluting particles, microparticles and nanoparticles). The stents may be intended for any vessel in the body, including neurological, carotid, vein graft, coronary, aortic, renal, iliac, femoral, popliteal vasculature, and urethral passages. A medical device can be designed for the localized delivery of a therapeutic agent.

DETAILED DESCRIPTION OF PREFERRED EMBODIMENTS OF THE INVENTION

Figure 1:
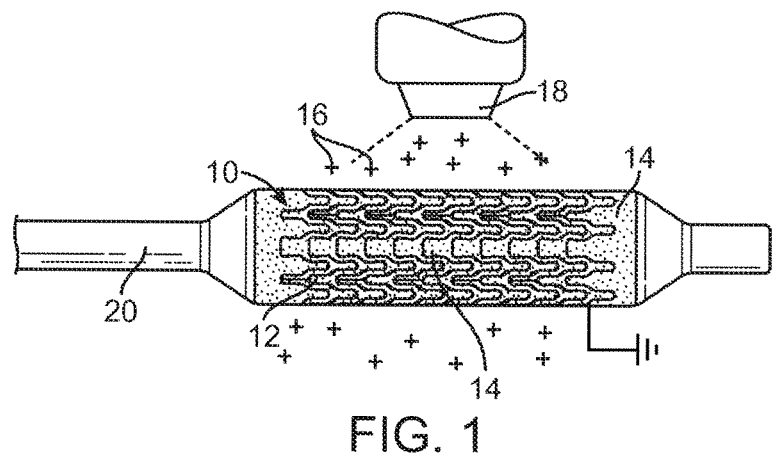
FIG. 1 is an illustration of a stent on a support device being electrostatically coated.

A method is provided for electrostatically coating stents having a polymeric component. As illustrated in FIG. 1, a stent 10 is supported by a mandrel or support structure 20. The mandrel or support structure 20 can be coupled to a driving means to provide rotational motion for spinning the stent 10 during electrostatic deposition. In one embodiment, the stent 10 can have a hollow, tubular body, including struts separated by gaps, as best illustrated by reference number 12 and 14, respectively. In other embodiments, the stent can be made from wires, fibers, coiled sheet, with or without gaps, or a scaffolding network of rings connected by arms. The stent can have any particular geometrical configuration, such as sinusoidal strut configuration, and should not be limited to what is illustrated in FIG. 1. The stent can be balloon expandable or self-expandable, both of which are well known in the art. The stent is preferably for cardiovascular use. In some embodiments, the stent can be for any bodily lumen such as the bile duct, urethra, etc.

The stent can be made from a polymeric material or polymer composites. This means that the struts 12, in and of themselves, are made from a polymer or combination of polymers and excludes any polymeric coatings on the stent.

In some embodiments, the stent can be metallic or polymeric and can include a polymeric coating or polymeric sheath or sleeve in which the stent is inserted. Accordingly, as defined herein, a "polymeric component" is intended to include the whole body of the stent, a part of the body of the stent, the struts, the sleeve/sheath, and/or the coating supported on the stent body substrate. Polymeric component, in some embodiments, may include a polymer composite such as for example a polymer or polymer combination including minor amounts of a metal such as a bioerodable metal. The coating can be a polymer primer layer attached to the stent surface and free from any drugs or active agents. The primer can provide for better adhesion of additional layers of polymers, drugs or other materials. The coating can alternatively be a top-coat layer deposited on a drug reservoir layer to, for example, reduce the rate of release of the drug. The drug reservoir layer can be a polymer free drug layer or can include a combination of a drug and polymer which have been mixed, blended, bonded or conjugated.

Figure 2:
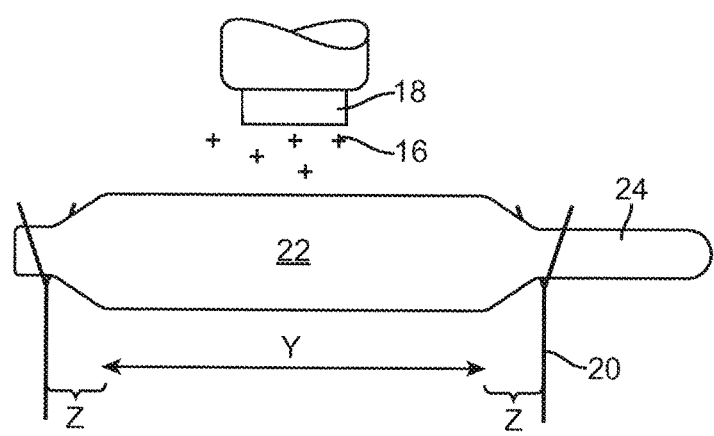
FIG. 2 is an illustration of a balloon on distal end of a catheter with a support or contacting element holding the balloon as the balloon is being electrostatically coated.

A method is provided for electrostatically coating balloons having a polymeric component. As illustrated in FIG. 2, a balloon 22 on distal end of a catheter 24 is supported by a contact device or support fixture 20. The contact or support fixture 20 can be coupled to a driving means to provide rotational motion for spinning the balloon 22 during electrostatic deposition. In one embodiment, the balloon 22 can have a working length Y and tapers Z. The balloon 22 can have any particular geometrical configuration, such as cylindrical, tapered, or pleated and should not be limited to what is illustrated in FIG. 2. The balloon 22 itself can be non-compliant or compliant, both of which are well known in the art. The balloon 22 is preferably for intravascular use. In some embodiments, the balloon 22 can be for any bodily lumen such as the bile duct, urethra, etc.

The balloon 22 can be made from a polymeric material or polymer composites. As for polymeric material from which the balloon can be made, preferred examples include polyethylene, polyurethanes, pellethanes, tecoflex®, tecothane®, silicones, polyesters, Hytrel, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides, nylon-6,6, nylon-12, nylon-6, polycaprolactam, poly(amide-co-ether), PEBAX amide-ether copolymer resins, polycarbonates, polyoxymethylenes, polyimides, polyethers, rayon, rayon-triacetate, cellulose, cellulose acetate, cellulose butyrate, cellulose acetate butyrate, cellophane, cellulose nitrate, cellulose propionate, and cellulose ethers.

In one embodiment, the polymeric material is compliant such as but not limited to a polyamide/polyether block copolymer (commonly referred to as PEBA or polyether-block-amide). The polyamide and polyether segments of the block copolymers may be linked through amide or ester linkages. The polyamide block may be selected from various aliphatic or aromatic polyamides known in the art. Some non-limiting examples include nylon 12, nylon 11, nylon 9, nylon 6, nylon 6/12, nylon 6/11, nylon 6/9, and nylon 6/6. Some non-limiting examples of polyether segments include poly(tetramethylene ether), tetramethylene ether, polyethylene glycol, polypropylene glycol, poly(pentamethylene ether) and poly(hexamethylene ether). Commercially available PEBA material may also be utilized such as for example, PEBAX® materials supplied by Arkema (France). Various techniques for forming a balloon from polyamide/polyether block copolymer is known in the art.

In another embodiment, the balloon material is formed from polyamides. Preferably, the polyamide has substantial tensile strength, be resistant to pin-holing even after folding and unfolding, and be generally scratch resistant, Some non-limiting examples of polyamide materials suitable for the balloon include nylon 12, nylon 11, nylon 9, nylon 69 and nylon 66.

In another embodiment, the balloon may be formed a polyurethane material, such as TECOTHANE® (Thermedics). TECOTHANE® is a thermoplastic, aromatic, polyether polyurethane synthesized from methylene disocyanate (MDI), polytetramethylene ether glycol (PTMEG) and 1,4 butanediol chain extender. Other suitable compliant polymeric materials include ENGAGE® (DuPont Dow Elastomers (an ethylene alpha-olefin polymer) and EXACT® (Exxon Chemical), both of which are thermoplastic polymers. Other suitable compliant materials include, but are not limited to, elastomeric silicones, latexes, and urethanes.

The compliant material may be cross linked or uncrosslinked, depending upon the balloon material and characteristics required for a particular application. For example, materials such as the polyolefinic polymers ENGAGE® and EXACT®, can be crosslinked. By crosslinking the balloon compliant material, the final inflated balloon size can be controlled. Conventional crosslinking techniques can be used including thermal treatment and E-beam exposure. After crosslinking, initial pressurization, expansion, and preshrinking, the balloon will thereafter expand in a controlled manner to a reproducible diameter in response to a given inflation pressure, and thereby avoid overexpanding the stent (when used in a stent delivery system) to an undesirably large diameter.

In one embodiment, the balloon is formed from a low tensile set polymer such as a silicone-polyurethane copolymer. Preferably, the silicone-polyurethane is an ether urethane and more specifically an aliphatic ether urethane such as PURSIL AL 575A and PURSIL AL10, (Polymer Technology Group), and ELAST-EON 3-70A, (Elastomedics), which are silicone polyether urethane copolymers, and more specifically, aliphatic ether urethane cosiloxanes. In an alternative embodiment, the low tensile set polymer is a diene polymer. A variety of suitable diene polymers can be used such as but not limited to an isoprene such as an AB and ABA poly(styrene-block-isoprene), a neoprene, an AB and ABA poly(styrene-block-butadiene) such as styrene butadiene styrene (SBS) and styrene butadiene rubber (SBR), and 1,4-polybutadiene. Preferably, the diene polymer is an isoprene including isoprene copolymers and isoprene block copolymers such as poly(styrene-block-isoprene). A presently preferred isoprene is a styrene-isoprene-styrene block copolymer, such as Kraton® 1161K available from Kraton, Inc. However, a variety of suitable isoprenes can be used including HT 200 available from Apex Medical, Kraton® R 310 available from Kraton, and isoprene (i.e., 2-methyl-1,3-butadiene) available from Dupont Elastomers. Neoprene grades useful in the invention include HT 501 available from Apex Medical, and neoprene (i.e., polychloroprene) available from Dupont Elastomers, including Neoprene G, W, T and A types available from Dupont Elastomers.

In some embodiments, the balloon can be composed of multiple layers of polymeric materials. Accordingly, as defined herein, a "polymeric component" is intended to include the whole body of the balloon, a part of the body of the balloon, the outermost layer of the balloon, and/or the coating supported on the balloon body substrate. Polymeric component, in some embodiments, may include a polymer composite such as, for example, a polymer or polymer combination including minor amounts of a metal, biodegradable metal, or a reinforcing material. The coating can be a polymer primer layer attached to the balloon surface and free from any drugs or active agents. The primer can provide for better adhesion of additional layers of polymers, drugs or other materials. The coating can alternatively be a top-coat layer deposited on a drug reservoir layer to, for example, reduce the rate of release of the drug. The drug reservoir layer can be a polymer free drug layer or can include a combination of a drug and polymer which have been mixed, blended, bonded or conjugated.

In accordance with another aspect of the invention, the outer surface of the medical device including a stent or balloon is physically modified. In this regard, the stent or balloon surface may include a textured surface, roughened surface, voids, spines, channels, dimples, pores, or microcapsules or a combination thereof. In another embodiment, the balloon includes protrusions configured to contact or penetrate the arterial wall of a vessel upon inflation of the balloon. When inflated or expanded, a therapeutic agent or coating containing therapeutic agent that is disposed on the protrusions is penetrated or pushed further into the tissue of the arterial wall.

The polymeric component can be durable, biodegradable, bioerodable, or bioabsorbable. Biodegradable, bioerodable, and bioabsorbable are terms used interchangeably and refer to polymers that are capable of being completely or substantially degraded or eroded when exposed to an in vivo environment or a representative in vitro. A polymeric component is capable of being degraded or eroded when it can be gradually broken-down, resorbed, absorbed and/or eliminated by, for example, hydrolysis, enzymolysis, oxidation, metabolic processes, bulk or surface erosion, and the like within a subject. In one embodiment, the stent is intended to fully biodegrade, in vivo, with the body of a mammal (e.g., human), in less than 2 years. In some embodiments, the time frame of full elimination of the stent is from 6 months to 14 months. The human can be an adult human between the ages of 30 and 85, preferably between 40 and 78.

As for polymeric material from which the stent can be made, preferred examples include poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluoropropylene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

As for coating materials, preferred examples include, poly(acrylates) such as poly(butyl methacrylate), poly(ethyl methacrylate), poly(hydroxylethyl methacrylate), poly(ethyl methacrylate-co-butyl methacrylate), copolymers of ethylene-methyl methacrylate, poly (2-acrylamido-2-methylpropane sulfonic acid), and polymers and copolymers of aminopropyl methacrylamide, poly(cyanoacrylates), poly(carboxylic acids), poly(vinyl alcohols), poly(maleic anhydride) and copolymers of maleic anhydride, fluorinated polymers or copolymers such as poly(vinylidene fluoride), poly(vinylidene fluoride-co-hexafluoropropylene), poly(tetrafluoroethylene), and expanded poly(tetrafluoroethylene), poly(sulfone), poly(N-vinyl pyrrolidone), poly(aminocarbonates), poly(iminocarbonates), poly(anhydride-co-imides), poly(hydroxyvalerate), poly(L-lactic acid), poly(L-lactide), poly(caprolactones), poly(lactide-co-glycolide), poly(hydroxybutyrates), poly(hydroxybutyrate-co-valerate), poly(dioxanones), poly(orthoesters), poly(anhydrides), poly(glycolic acid), poly(glycolide), poly(D,L-lactic acid), poly(D,L-lactide), poly(glycolic acid-co-trimethylene carbonate), poly(phosphoesters), poly(phosphoester urethane), poly(trimethylene carbonate), poly(iminocarbonate), poly(ethylene), poly(propylene) co-poly(ether-esters) such as, for example, poly(dioxanone) and poly(ethylene oxide)/poly(lactic acid), poly(anhydrides), poly(alkylene oxalates), poly(phosphazenes), poly(urethanes), silicones, poly(esters), poly(olefins), copolymers of poly(isobutylene), copolymers of ethylene-alphaolefin, vinyl halide polymers and copolymers such as poly(vinyl chloride), poly(vinyl ethers) such as poly(vinyl methyl ether), poly(vinylidene halides) such as, for example, poly(vinylidene chloride), poly(acrylonitrile), poly(vinyl ketones), poly(vinyl aromatics) such as poly(styrene), poly(vinyl esters) such as poly(vinyl acetate), copolymers of vinyl monomers and olefins such as poly(ethylene-co-vinyl alcohol) (EVAL), copolymers of acrylonitrile-styrene, ABS resins, and copolymers of ethylene-vinyl acetate, poly(amides) such as Nylon 66 and poly(caprolactam), alkyd resins, poly(carbonates), poly(oxymethylenes), poly(imides), poly(ester amides), poly(ethers) including poly(alkylene glycols) such as, for example, poly(ethylene glycol) and poly(propylene glycol), epoxy resins, polyurethanes, rayon, rayon-triacetate, biomolecules such as, for example, fibrin, fibrinogen, starch, poly(amino acids), peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans, other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose, and derivatives, analogs, homologues, congeners, salts, copolymers and combinations thereof. Other examples that can be used include polycaprolactones, poly(D,L-lactide-co-PEG) block copolymers, poly(D,L-lactide-co-trimethylene carbonate), polyglycolides, poly(lactide-co-glycolide), poly(amino acids), polycyanoacrylates, poly(trimethylene carbonate) polycarbonates, polyurethanes, copoly(ether-esters) (e.g. PEO/PLA), polyalkylene oxalates, PHA-PEG, and any derivatives, analogs, homologues, salts, copolymers and combinations thereof.

A treatment composition is applied to the polymeric component. In some embodiments the treatment composition includes a halogen, halide, or a complex or salt thereof. Iodine, bromine, chlorine and fluorine can be used. In the most preferred embodiment, iodine, iodide, or iodate is used. Complexes of halogen or halides can include those with biobeneficial polymers such as polyethylene glycol (PEG). PEG is a well know bio-friendly polymer that has been reported to have beneficial use with stents. As another example, poly(N-vinyl pyrrolidone) can be used. Other suitable polymers to use with iodide or iodate salts in stent or balloon coatings are poly(vinyl alcohol), poly(2-hydroxyethyl methacrylate), poly(N-(2-hydroxypropyl) methacrylamide), chitosan, hyaluronic acid, chondroitin sulfate, and poly(ethylene glycol-co-propylene glycol) copolymers (known as PLURONIC), poly(acrylates) such as poly(butyl methacrylate), poly(ethyl methacrylate), poly(ethyl methacrylate-co-butyl methacrylate), copolymers of ethylene-methyl methacrylate, poly(2-acrylamido-2-methylpropane sulfonic acid), and polymers and copolymers of aminopropyl methacrylamide, poly(cyanoacrylates), poly(maleic anhydride) and copolymers of maleic anhydride, fluorinated polymers or copolymers such as poly(vinylidene fluoride), poly(vinylidene fluoride-co-hexafluoropropylene), poly(sulfone), poly(aminocarbonates), poly(anhydride-co-imides), poly(hydroxyvalerate), poly(L-lactic acid), poly(L-lactide), poly(caprolactones), poly(lactide-co-glycolide), poly(hydroxybutyrates), poly(hydroxybutyrate-co-valerate), poly(dioxanones), poly(orthoesters), poly(anhydrides), poly(glycolic acid), poly(glycolide), poly(D,L-lactic acid), poly(D,L-lactide), poly(glycolic acid-co-trimethylene carbonate), poly(phosphoesters), poly(phosphoester urethane), poly(trimethylene carbonate), poly(iminocarbonate), poly(ethylene), poly(propylene) co-poly(ether-esters) such as, for example, poly(dioxanone) and poly(ethylene oxide)/poly(lactic acid), poly(anhydrides), poly(alkylene oxalates), poly(phosphazenes), poly(urethanes), silicones, poly(esters), poly(olefins), copolymers of poly(isobutylene), copolymers of ethylene-alphaolefin, vinyl halide polymers and copolymers such as poly(vinyl chloride), poly(vinyl ethers) such as poly(vinyl methyl ether), poly(vinylidene halides) such as, for example, poly(vinylidene chloride), poly(acrylonitrile), poly(vinyl ketones), poly(vinyl aromatics) such as poly(styrene), poly(vinyl esters) such as poly(vinyl acetate), copolymers of vinyl monomers and olefins such as poly(ethylene-co-vinyl alcohol) (EVAL), copolymers of acrylonitrile-styrene, ABS resins, and copolymers of ethylene-vinyl acetate, poly(amides) such as Nylon 66 and poly(caprolactam), alkyd resins, poly(carbonates), poly(oxymethylenes), poly(imides), poly(ester amides), poly(ethers) including poly(alkylene glycols) such as, for example, poly(ethylene glycol) and poly(propylene glycol), epoxy resins, polyurethanes, rayon, rayon-triacetate, biomolecules such as, for example, fibrin, fibrinogen, starch, poly(amino acids), peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans, other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose, and derivatives, analogs, homologues, congeners, salts, copolymers and combinations thereof. Other examples that can be used include polycaprolactones, poly(D,L-lactide-co-PEG) block copolymers, poly(D,L-lactide-co-trimethylene carbonate), polyglycolides, poly(lactide-co-glycolide), poly(amino acids), polycarbonates, polyurethanes, copoly(ether-esters) (e.g. PEO/PLA), polyalkylene oxalates, PHA-PEG, and any derivatives, analogs, homologues, salts, copolymers and combinations thereof. In the case of iodide and iodate salts, preferred counterions are lithium, sodium, benzalkonium, ammonium, ethanolamine, diethanolamine, imidazole, meglumine, tridodecylmethyl ammonium, cationic lipids, and potassium. Complexes may also include non-ionic, anionic, cationic and amphoteric surfactants—which may improve solubility of the halogen.

For a drug coated balloon, the coating can be completely soluble, and as such, it may contain only biocompatible excipients. Suitable surfactant excipients to combine with a halogen, halide, or a complex or salt thereof (e.g., iodine, iodide, iodate, salts, etc.) are Tween® 20 (polysorbate 20), Tween® 60 (polysorbate 60), Tween® 80 (polysorbate 80), Vitamin E TPGS, Pluronic® F68, Pluronic® F127, Poloxamer 407, Ascorbyl palmitate, gelatin, lecithin, egg yolk phopholipid, phosphatidylcholine, polyethylene glycol-phosphatidyl ethanolamine conjugate, (PEG-PE), other PEG-Phospholipid conjugates. Polysorbates are a group of oleate esters of sorbitol and its' anhydrides condensed with polymers of ethylene oxide. Examples include polysorbate 20, polysorbate 60, and polysorbate 80 the specifications of which are all listed in the United States Pharamcopeia (USP). Poloxamers are tri-block copolymers with a central block of poly(propylene oxide) (PPO) and with a block of poly(ethylene oxide) (PEO) on each side where the PEO blocks are usually of the same length in terms of number of constitutional units. Poloxamers of types 124, 188, 237, 338, and 407 are specified by a monograph in the National Formulary. Pluronic® is a trade name for poly(ethylene oxide)—poly (propylene oxide) block copolymers produced by BASF. Other plasticizing components to combine with iodine, iodide, iodate, salts, or complexes, with or without a polymer, are benzyl alcohol, benzyl benzoate, ethanol, DMSO, NMP, glycerol, propylene glycol, Cremophor EL, Vitamin E, Tocopherols, PEG with MW less than 1000, ethyl lactate, soybean oil, peanut oil, liquid PEG, poppyseed oil, safflower oil, vegetable oil, cottonseed oil, castor oil, and almond oil. Halide containing compounds are known in the art and readily identifiable by one or ordinary skill in the art.

The treatment composition can be applied in liquid form by immersing the device in the treatment composition or spraying the device with the treatment composition. Brushing techniques can also be used. The liquid form can be accomplished by having a carrier or solvent, for example water, an alcohol such as ethanol, isopropanol, and methanol, or an ether. The following solvents have been shown to provide acceptable use in coating stents and balloons and can be used with the embodiments of the invention: DMAC, DMF, THF, cyclohexanone, xylene, toluene, acetone, methanol, ethanol, i-propanol, n-butanol, methyl ethyl ketone, propylene glycol monomethyl ether, methyl butyl ketone, ethyl acetate, n-butyl acetate, hexane, pentane, octane, and dioxane. A combination of any of these can also be used.

The concentration of halogen, halide or halogen (iodine, iodide, iodate, complexes, salts, etc.) containing compound can be from 0.1% to 90%. It can be from 1% to 20%. In some embodiments, the halogen or halide containing compound, including complexes and salts, is kept on a stent and not washed out. Accordingly, an added benefit can be provided, namely imparting visualization properties to the stent. With the use of iodine, for example, in one embodiment, the concentration should be high enough to also impart visual capabilities from an imagining device to the stent (or balloon) when the stent (or balloon) is used in during the medical procedure. Sufficient amount of iodine will allow the physician to be able to see the stent (or balloon) during delivery and implantation procedure.

Following the application of the treatment composition, the stent can be grounded (FIG. 1) or a charge can be applied. Charged drug particles 16, having opposite charge or polarity than the stent, should the stent be charged, are then bombarded at the stent. Application by the charged drug can be by a nozzle 18 via spray application. FIG. 1 illustrates the drug being positively charged and the stent grounded. Alternatively a negative charge can be applied to the stent or the drug can be negatively biased or polarized and the stent positively biased or polarized. The charged drug particles can be applied while the surface is wet or dry, or any point in between. In other words, the solvent of the treatment composition, if used, can be extracted or semi-extracted such as by evaporation before the charged drug particles are applied.

The above described procedure can be similarly followed for a balloon, as illustrated by FIG. 2.

Both liquids and dry powders can be electrostatically coated. The drug can be in a solvent carrier, such as those mentioned above, or in a dry, powdered form. The present invention is not limited to drugs as other agents and polymers can be coated using the methods of the present invention. In one embodiment, a combination of a polymer and a drug can be electrostatically coating on the polymeric component of the stent. The polymers can be those previously listed.

As a final step, if opted, a baking treatment can be employed. The stent or balloon can be placed in an oven under suitable temperature that does not adversely affect the drug or other components.

Examples of drugs that can be coated on stents using the method of the present invention include any moiety capable of contributing to a therapeutic effect, a prophylactic effect, both a therapeutic and prophylactic effect, or other biologically active effect in a mammal. An agent can also be coated which has a diagnostic property. The drug or bioactive agents include, but are not limited to, small molecules, nucleotides, oligonucleotides, polynucleotides, amino acids, oligopeptides, polypeptides, and proteins. In one example, the drug or bioactive agent inhibits the activity of vascular smooth muscle cells. In another example, the drug or bioactive agent controls migration or proliferation of smooth muscle cells to prevent or inhibit restenosis.

Bioactive agents include, but are not limited to, antiproliferatives, antineoplastics, antimitotics, anti-inflammatories, antiplatelets, anticoagulants, antifibrins, antithrombins, antibiotics, antiallergics, antioxidants, and any prodrugs, metabolites, analogs, homologues, congeners, derivatives, salts and combinations thereof.

Antiproliferatives include, for example, actinomycin D, actinomycin IV, actinomycin $I_1$, actinomycin $X_1$, actinomycin $C_1$, dactinomycin (COSMEGEN®, Merck & Co., Inc.), imatinib mesylate, and any prodrugs, metabolites, analogs, homologues, congeners, derivatives, salts and combinations thereof. Antineoplastics or antimitotics include, for example, paclitaxel (TAXOL®, Bristol-Myers Squibb Co.), docetaxel (TAXOTERE®, Aventis S.A.), methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), midostaurin, and any prodrugs, metabolites, analogs, homologues, congeners, derivatives, salts and combinations thereof.

Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof.

Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other bioactive agents that are preferably used in the present invention include, but are not limited to, free radical scavengers; nitric oxide donors; rapamycin; methyl rapamycin; 42-Epi-(tetrazoylyl)rapamycin (ABT-578); 40-O-(2-hydroxy)ethyl-rapamycin (everolimus); biolimus, myolimus, novolimus, temsirolimus, deforolimus, tacrolimus; pimecrolimus; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329, 386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

Examples of diagnostic agents include radiopaque materials and include, but are not limited to, materials comprising iodine or iodine-derivatives such as, for example, iohexyl and iopamidol, which are detectable by x-rays. Other diagnostic agents such as, for example, radioisotopes, are detectable by tracing radioactive emissions. Other diagnostic agents may include those that are detectable by magnetic resonance imaging (MRI), ultrasound and other imaging procedures such as, for example, fluorescence and positron emission tomography (PET). Examples of agents detectable by MRI are paramagnetic agents, which include, but are not limited to, gadolinium chelated compounds. Examples of agents detectable by ultrasound include, but are not limited to, perflexane. Examples of fluorescence agents include, but are not limited to, indocyanine green. Examples of agents used in diagnostic PET include, but are not limited to, fluorodeoxyglucose, sodium fluoride, methionine, choline, deoxyglucose, butanol, raclopride, spiperone, bromospiperone, carfentanil, and flumazenil.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. However, it is intended that all such variations not departing from the spirit of the invention be considered as within the scope thereof.

What is claimed is:

1. A method of manufacturing a drug coated stent, comprising:
mounting a stent on a support structure, the stent being made from a polymeric material having insufficient conductivity for electrostatic coating;
forming a treatment composition comprising a surfactant, and iodine, iodide, iodate, a complex or salt thereof;
applying the treatment composition to a surface of the stent;
applying a first charge to the stent or grounding the stent after the application of the treatment composition comprising the iodine, iodide, iodate, the complex or salt thereof to the surface of the stent; and
applying a drug having a charge to the stent such that the drug is electrostatically deposited on the stent;
wherein the surfactant is selected from the group consisting of polysorbate 20, polysorbate 60, polysorbate 80, Vitamin E TPGS, Poloxamer 407, Ascorbyl palmitate, gelatin, lecithin, egg yolk phopholipid, phosphatidylcholine, polyethylene glycol-phosphatidyl ethanolamine conjugate (PEG-PE), and combinations thereof.

2. The method of claim 1, wherein the iodine, iodide, iodate, the complex or salt thereof remains on the stent and the amount remaining on the stent allows for visualization of the stent by a physician during a stent implantation procedure.

3. The method of claim 1, additionally comprising applying a charged polymer contemporaneously with the application of the charged drug.

4. The method of claim 1, wherein the drug is selected from the group consisting of rapamycin, methyl rapamycin, everolimus, zotarolimus, biolimus, temsirolimus, myolimus, novolimus, ridaforolimus, tacrolimus, paclitaxel, protaxel, docetaxel, estradiol, clobetasol, idoxifen, tazarotene, and combinations thereof.

5. The method of claim 1, additionally comprising rotating the support structure to rotate the stent during electrostatic deposition of the drug.

6. The method of claim 1, wherein the complex of iodine, iodide, or iodate is a polymer complex.

7. The method of claim 6, wherein the polymer of the complex is polyethylene glycol, poly(N-vinyl pyrrolidone), or a combination thereof.

8. The method of claim 1, wherein the drug is in a liquid form.

9. The method of claim 1, wherein the surfactant is selected from the group consisting of Vitamin E TPGS, Ascorbyl palmitate, gelatin, lecithin, egg yolk phopholipid, phosphatidylcholine, polyethylene glycol-phosphatidyl ethanolamine conjugate (PEG-PE), and combinations thereof.

10. The method of claim 1, wherein the treatment composition comprises a plasticizing component.

11. The method of claim 10, wherein the plasticizing component is selected from the group consisting of benzyl alcohol, benzyl benzoate, ethanol, DMSO, NMP, glycerol, propylene glycol, Cremophor EL, Vitamin E, Tocopherols, PEG with MW less than 1000, ethyl lactate, soybean oil, peanut oil, liquid PEG, poppyseed oil, safflower oil, vegetable oil, cotton-seed oil, castor oil, almond oil, and combinations thereof.

* * * * *